United States Patent [19]

Vanhoof et al.

[11] 3,981,872

[45] Sept. 21, 1976

[54] DERIVATIVES OF 2-AMINO-(1,2,3,4-TETRAHYDRONAPHTHALENE)

[75] Inventors: Pierre M. Vanhoof; Pierre M. Clarebout, both of Brussels, Belgium

[73] Assignee: A. Christiaens Societe Anonyme, Brussels, Belgium

[22] Filed: Dec. 6, 1974

[21] Appl. No.: 530,095

Related U.S. Application Data

[62] Division of Ser. No. 404,048, Oct. 5, 1973, Pat. No. 3,943,172.

[30] Foreign Application Priority Data

Oct. 6, 1972   United Kingdom............... 46268/72

[52] U.S. Cl.................. 260/247.2 A; 260/247.5 R; 260/268 BC; 260/326.33; 260/326.85; 260/562 N; 260/570.8 R; 424/248; 424/250; 424/267; 424/274; 424/324; 424/330; 260/570.5 P

[51] Int. Cl.²...................................... C07D 295/14

[58] Field of Search............... 260/293.62, 247.2 A, 260/247.5 R, 268 BC, 326.33, 326.85

[56] References Cited
UNITED STATES PATENTS

3,737,455   6/1973   Shen et al........................... 260/520

*Primary Examiner*—G. Thomas Todd
*Attorney, Agent, or Firm*—Sughrue, Rothwell, Mion, Zinn and Macpeak

[57] ABSTRACT

This invention relates to new derivatives of 2-amino-(1,2,3,4-tetrahydronaphthalene), namely 2-[N-phenyl-N-($R_1$,$R_2$-aminoalkyl or alkanoyl)]-amino-(1,2,3,4-tetrahydronaphthalenes), in which $R_1$ and $R_2$ represent a lower alkyl group or form together with the attached nitrogen atom a nitrogenous heterocyclic ring, with the proviso that $R_1$ may also represent hydrogen, as well as to the acid addition salts of these new derivatives.

These new derivatives are active for the treatment of heart arrhythmy.

1 Claim, No Drawings

3,981,872

DERIVATIVES OF 2-AMINO-(1,2,3,4-TETRAHYDRONAPHTHALENE)

This is a division of application Ser. No. 404,048, filed Oct. 5, 1973, now U.S. Pat. No. 3,943,172.

BRIEF DESCRIPTION OF THE INVENTION

This invention relates to new derivatives of 2-amino-(1,2,3,4-tetrahydronaphthalene), to the preparation and to the use thereof.

The new derivatives of 2-amino-(1,2,3,4-tetrahydronaphthalene) are 2-[N-phenyl-N-($R_1$, $R_2$-aminoalkyl or alkanoyl)]-amino-(1,2,3,4-tetrahydronaphthalene) of the general formula:

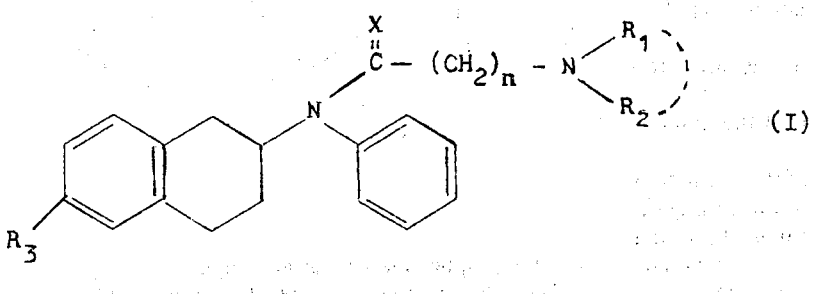

in which $n = 1$ or 2, X represents two hydrogen atoms or one oxygen atom, $R_1$ and $R_2$ represent a lower alkyl group containing 1 to 4 carbon atoms or form together with the attached nitrogen atom a nitrogenous heterocyclic ring, with the proviso that $R_1$ may also represent hydrogen, and $R_3$ represents hydrogen or a lower alkoxy group, as well as the acid addition salts of said compounds of formula (I).

The preferred compounds of the formula (I) are those in which $R_1$ and $R_2$ represent a methyl, ethyl, propyl or isopropyl group and these in which $R_1$ represents hydrogen and $R_2$ represents a methyl, ethyl, propyl or isopropyl group, as well as the acid addition salts thereof, such as the hydrochlorides, fumarates, oxalates, etc.

This invention relates also to pharmaceutical compositions containing as active ingredient, at least one compound of the general formula (I), together with a pharmaceutically acceptable carrier.

Finally, the invention relates to processes for preparing the new compounds of formula (I).

DETAILED DESCRIPTION OF THE INVENTION

It has been surprisingly found that the compounds of the general formula (I) are very active for the treatment of heart arrhythmia.

Said compounds can be used for the treatment of various heart diseases such as premature heart contractions, ventricular and supraventricular tachycardias either idiopathic or subsequent to a cardiopathia or to a coronary disease, cardiac arrhythmias due to digitalin intoxication, as well as atrial fibrillation and flutter, particularly in the early stage.

It is known (see Koch-Weser, J. Arch. Int. Med. 129; 763, 1972) that none of the presently available antiarrhythmic agents are satisfactory for the prophylaxis of tachycardias and fibrillation of ventricular origin.

The oral activity of the known antiarrhythmic agents, such as procainamide or lidocaine, is either too short leading to multiple day and night administration (for example with procainamide) or too low to be of some practical utility (for example with lidocaine) or their therapeutic activity is conjugated with frequent and dangerous side effects, such as hypotension (with procainamide), sudden death, agranulocytosis or idiosyncrasy.

The compounds of general formula (I) according to this invention are very active when orally administered, although they may also be administered parenterally. They have also a long activity duration and are not depressant for the myocardial function.

Applicants do not know any orally active antiarrhythmic agent which does not act at the same time as a depressant of the myocardial function.

The oral antiarrhythmic activity of the compounds of formula (I) has been proved by tests on rats using econitine which is a compound causing premature heart contractions and death of the animals.

The method used for these tests is described hereafter:

Animals:

Male or female rats with a body-weight ranging from 380 to 450 g.

Aconitine solution:

3.12 μg aconitine nitrate/1 ml physiological saline.

Solution of the compound to be tested:

0.75 % in distilled water.

Method:

Six random selected animals are required for each compound to be tested. The compound is administered by oral route at the dose of 75 mg/kg (1 ml of the 0.75 % solution/100 g of body-weight) 75 minutes before the intravenous perfusion of the aconitine solution is initiated.

Control groups of animals are treated only with distilled water (1 ml/100 g).

Sixty minutes after the administration of the compound to be tested, the animals are anesthesized by an intraperitoneal injection of Pentobarbital (50 mg/kg) and the jugular vein is dissected.

A catheter is introduced in the vein and fixed by a ligature.

The ECG (D II derivation) is then continuously recorded. The perfusion of the aconitine solution is started 75 minutes after the administration of the compound to be tested. The volume delivered by the injection device being 0.287 ml/minue, the dose of aconitine nitrate administered is 0.895 μg/minute (0.20 – 0.24 μg/100 g/minute according to the minimal and maximal weight of the animals).

The experience is stopped as soon as the first extrasystoles are appearing and the time elapsed from the beginning of the perfusion is noted.

The results are expressed as the mean total dose of aconitine injected in a group of animals.

The relative activity between a tested compound and a reference substance (lidocaine, procainamide) is computed in the following way:

$$A(x) = \frac{\overline{X} - \overline{C}}{\overline{R} - \overline{C}} \times 100$$

where:

$A(x)$ = activity of tested compound X (in %)
$\overline{X}$ = mean dose of aconitine in the animals treated by compound X
$\overline{C}$ = mean dose of aconitine injected in the untreated animals (controls)
$\overline{R}$ = mean dose of aconitine injected in the animals treated by the reference substances.

The following table gives the results of the evaluation of the antiarrhythmic activity by oral route of a great number of acid addition salts of compounds of formula (I), compared to the activity of two well known antiarrhythmic agents (procainamide and lidocaine).

TABLE 1

| Compounds of formula I | | | % activity versus | |
|---|---|---|---|---|
| X | $R_3$ | $-N\langle{}^{R_1}_{R_2}$ | Lidocaine | Procainamide |
| $H_2$ | H | N-diethyl | 439 | 560 |
| $H_2$ | H | NH-ethyl | 288 | 368 |
| $H_2$ | H | NH-ethyl | 703 | 897 |
| $H_2$ | H | N-dimethyl | 41 | 52 |
| $H_2$ | H | N-diethyl | 563 | 719 |
| $H_2$ | H | piperidino | 62 | 78 |
| $H_2$ | H | pyrrolidino | 268 | 342 |
| O | H | NH-methyl | 769 | 982 |
| $H_2$ | $OCH_3$ | N-dimethyl | 57 | 72 |
| $H_2$ | $OCH_3$ | piperidino | 103 | 131 |
| $H_2$ | $OCH_3$ | N-diethyl | 173 | 220 |
| $H_2$ | $OCH_3$ | N-diethyl | 96 | 123 |

The compounds of the formula (I) may be administered orally or parenterally.

Oral preparations may be administered under the form of capsules, tablets, pills and the like. Each capsule, tablet or pill may contain from 10 to 200 mg of a compound of formula (I) as active ingredient, together with pharmaceutically acceptable excipients or carriers.

Parenteral preparations may consist in a solution for perfusion or for intravenous or intramuscular injection. Such a solution may contain from 0.2 per thousand to 2 per thousand of a compound of formula (I).

The parenteral preparation may be either a solution which may be directly used for the perfusion and contains a proportion of the active ingredient within the above limits, or a concentrated solution containing 1 to 10 % of the active ingredient, said concentrated solution being diluted when administered to a patient.

The initial dose of active ingredient may be of 200 to 800 mg per day during 2 or 3 days, the maintenance dose being of about 25 mg to 300 mg per day.

If a single dose is sufficient for obtaining the therapeutic affect, this dose is generally comprised between 50 and 300 mg.

The active ingredient may be administered at the same time by the parenteral route (for example by perfusion) and by the oral route.

This invention relates also to processes for preparing the compounds of formula (I).

In the various processes described hereinafter, the compounds of formula (I) are prepared from a 2-(phenylamino)-(1,2,3,4-tetrahydronaphthalene) of the following formula:

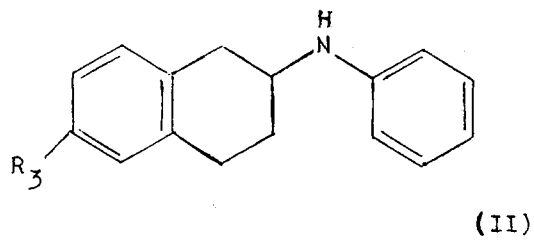

(II)

in which $R_3$ has the above meanings.

According to this invention, the compounds of formula (I) may be prepared by a first process involving the following steps:

1. Conversion of a 2-(phenylamino)-(1,2,3,4-tetrahydronaphthalene) of formula (II) into the sodium salt thereof by reaction with sodium amide.
2. Reaction of the sodium salt of the compound of formula (II) with a halogenated amine of the formula:

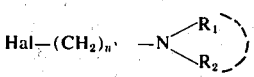

in which Hal represents a halogen atom and $n' = 2$ or 3, whereas $R_1$ and $R_2$ have the above meanings, so as to obtain a compound of formula (I).

According to this invention, the compounds of formula (I) may also be prepared by a second process involving the following steps:

1. Acylation of 2-(phenylamino)-(1,2,3,4-tetrahydronaphthalene) of formula (II) by means of a chloride of a halogenated aliphatic acid of the formula:

Hal $(CH_2)_n$ - COCl      IV.

in which Hal represents a halogen atom and $n = 1$ or 2, so as to obtain a 2-(N-haloalkanoyl-N-phenylamino)-(1,2,3,4-tetrahydronaphthalene) of the formula:

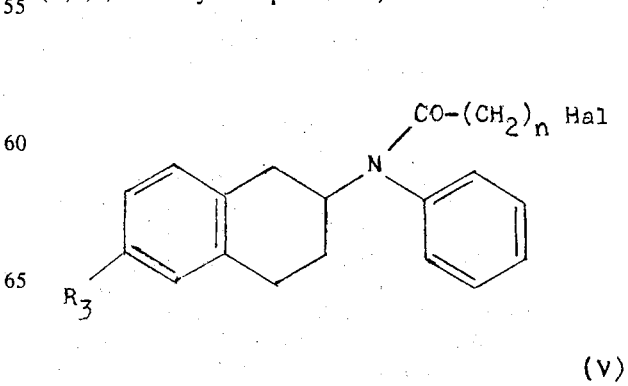

(V)

2. Reaction of the 2-(N-haloalkanoyl-N-phenylamino)-(1,2,3,4-tetrahydronaphthalene) of formula (V) with an amine of the formula:

in which $R_1$ and $R_2$ have the above meanings, so as to obtain a N-alkylated derivative of the following formula:

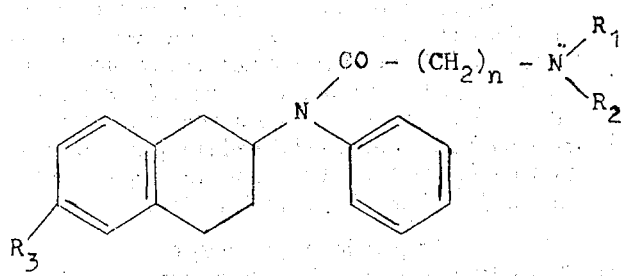

3. Reduction of the compound of formula (VII) by means of lithium aluminum hydride ($AlLiH_4$) in ether so as to obtain a compound of the formula (I), wherein X represents two halogen atoms.

The amine of formula (VI) used in the second step of the above process may be a primary or secondary amine.

A primary amine of the formula $H_2NH_2$ is used, when a compound of the formula (I), in which $R_1$ represents hydrogen whereas $R_2$ represents a lower alkyl group has to be prepared.

A secondary amine of the formula:

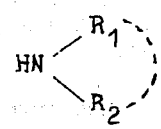

is used, when a compound of the formula (I), in which $R_1$ and $R_2$ each represent a lower alkyl group or form together with the attached nitrogen atom a heterocyclic nitrogenous ring, such as morpholino, piperidino, pyrrolidino or piperamine ring, has to be prepared.

The 2-(N-phenylamino)-(1,2,3,4-tetrahydronaphthalenes) of the formula (II) may be prepared from β-tetralones of the formula:

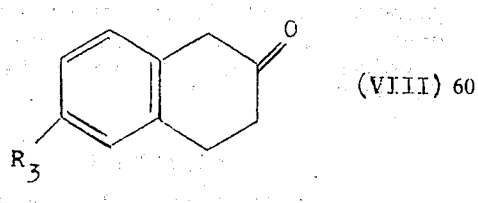

in which $R_3$ has the above meanings.

The compounds of formula (VIII) may be prepared by knows methods described by J. H. Burckalter, J. R. Campbell, J.O.C., 26, 4232 (1961), by A. Rosowsky, J. Battaglia, K.K.N. Chen and E. J. Modest, J.O.C., 33, 4288 (1968) or by J. J. Sims, L. H. Selman, M. Cadogan, Org. Synth., 51, 109 (1971).

The method for obtaining a 2-(N-phenylamino)-(1,2,3,4-tetrahydronaphthalene) of formula (II) from a β-tetralone of formula (VIII) involves the following steps:

1. Reduction of a β-tetralone of the formula (VIII) into a 2-hydroxy-(1,2,3,4-tetrahydronaphthalene) of formula (IX) by means of sodium boron hydride in methanol:

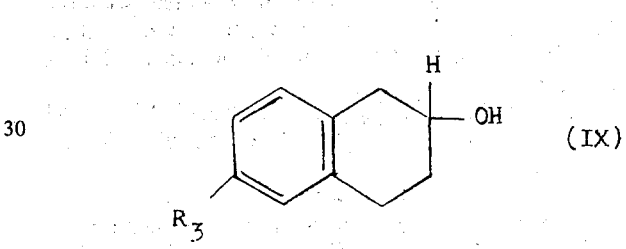

2. Conversion of the 2-hydroxy-(1,2,3,4-tetrahydronaphthalene) of formula (IX) into the mesylate thereof of formula (X) by means of methane sulfonic acid chloride in pyridine:

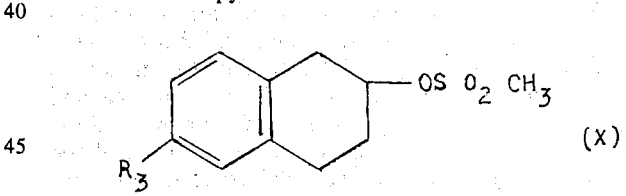

3. Reaction of the mesylate of formula (X) with an excess of aniline so as to obtain a 2-(phenylamino)-(1,2,3,4-tetrahydronaphthalene) of the formula (II).

EXAMPLES

The following Examples 1 to 18 illustrate the preparation of new compounds of formula (I)

EXAMPLE 1

Preparation of the fumarate and oxalate of 2-[N-phenyl-N-(γ-diethylaminopropyl)]-amino-(1,2,3,4-tetrahydronaphthalene)

(formula I; n = 2; X = $H_2$; $R_1 = R_2 = -C_2H_5$; $R_3 = H$).

a. Preparation of the mesylate of β-tetralol (formula IX; $R_3$=H).

15.38 grams (0.104 mol) of β-tetralol are placed in 15.8 ml of pyridine. The solution is cooled to 0°C and 1.2 equivalents of mesyl chloride ($ClSO_2CH_3$) are added, while stirring, the temperature being maintained at 0°C during the addition. The reaction mixtue is then allowed to return to the room temperature and is stirred at this temperature during 30 minutes. The mixture is then poured on ice and kept during one night in a refrigerator. The obtained precipitate (21.44 grams; yield: 90 %) is separated by filtration and recrystallized from sulphuric ether. Melting point: 62–64°C.

Analysis: % calculated: C 58.38; H 6.23. % found: C 58.67; H 6.31.

b. Preparation of the hydrochloride of 2-phenylamino-(1,2,3,4-tetrahydronaphthalene) (formula II; $R_3 = H$).

0.096 mol of the mesylate of β-tetralol are mixed with 35.8 grams of aniline. The mixture is quickly heated to 130°C and maintained at this temperature during 30 minutes. After cooling and addition of about 200 ml of ether, the aniline mesylate is filtered off. The ether is then removed from the filtrate and the excess of aniline is distilled. By distilling the residue, 11.28 grams (yield: 52 %) of the desired product are obtained at 149°–151°C/0.4 mm. The product is dissolved in 50 ml of anhydrous methanol and a stream of dry hydrochloric acid is passed through the obtained solution. The obtained hydrochloride is purified by crystallization from a mixture of methanol and ether. Melting point: 193°–196°C.

Analysis: % calculated: C 73.97 H 6.98; N 5.39; Cl 13.65. % found: C 74.2; H 7.00; N 5.51; Cl 13.7.

c. Preparation of the fumarate of 2-[N-phenyl-N-(γ-diethylaminopropyl)]-amino-(1,2,3,4-tetrahydronaphthalene) (formula I; n = 2; X = $H_2$; $R_1 = R_2 = -C_2H_5$; $R_3 = H$).

100 ml of anhydrous toluene containing 11.2 grams (0.05 mol) of 2-phenylamino-1,2,3,4-tetrahydronaphthalene and 3.9 grams (0.1 mol) of $NaNH_2$ are refluxed during 20 minutes. 8.94 grams (0.06 mol) of γ-chloropropyldiethylamine are then added and the mixture is refluxed during 3 hours. After cooling, the mixture is extracted by means of 2N hydrochloric acid. The acid phase is made alkaline by means of ammonia and extracted with ether. The ether phase is dried and the ether is then removed. The obtained residue is converted into a fumarate by means of an aqueous solution of fumaric acid. The obtained solution is evaporated to dryness and the residue is extracted with a mixture of methanol and ether, 8.55 grams (yield : 43 %) of the fumarate are obtained. Melting point: 134°–136°C.

Analysis: The analysis shows that the fumarate comprises 1 equivalent of the amine of formula (I) and 0.5 equivalent of fumaric acid. % calculated: C 76.1; H 8.68; N 7.10. % found: C 76.46; H 8.70; N 7.34.

d. Oxalate of 2-[N-phenyl-N-(γ-diethylaminopropyl)]-amino(1,2,3,4-tetrahydronaphthalene) (formula I; n = 2 ; X =$H_2$; $R_1 = R_2 = -C_2H_5$; $R_3 = H$).

The oxalate prepared as described in section C of this example, by using oxalic acid in place of fumaric acid melts at 155°–157°C after recrystallization from acetone.

Analysis: % calculated: C 70.39; H 8.03; N 6.56. % found: C 70.22; H 8.06; N 6.66.

EXAMPLE 2

Preparation of the fumarate of 2[N-phenyl-N-(γ-diethylaminopropyl)]-amino-6-methoxy-(1,2,3,4-tetrahydronaphthalene) (formula I; n = 2; X = $H_2$; $R_1 = R_2 = -C_2H_5$; $R_3 = -OCH_3$).

a. Preparation of 2-hydroxy-6-methoxy-1,2,3,4-tetrahydronaphthalene (formula IX; $R_3 = -OCH_3$).

4.99 grams (0.132 mol) of $NaHB_4$ are gradually added to a solution of 21.24 grams of 6-methoxy-β-tetralone (formula VIII; $R_3 = -OCH_3$) (0.12 mol) in 130 ml of anhydrous methanol. This addition takes place under a slight reflux. After 17 hours at room temperature, the methanol is removed and the residue is extracted with 150 ml of cool water. The obtained solution is acidified to a pH of 5–6 and extracted with ether. After washing of the ether phase with 50 ml of water, the ether phase is dried and the ether is evaporated. By distillation at 110°–115°C/0.4 mm, 15.58 grams of the desired alcohol are obtained (yield: 73 %).

b. Preparation of the mesylate of 2-hydroxy-6-methoxy-1,2,3,4-tetrahydronaphthalene (formula X; $R_3 = -OCH_3$).

This compound is prepared as described in Example 1(a) from a mixture of 15.58 grams of the alcohol of formula (IX), 15.58 grams of pyridine and 12.02 grams of mesyl chloride.

17 grams (yield: 75.8 %) of the desired mesylate are obtained. After recyrstallization from ether, the product melts at 78°–80°C.

Analysis: % calculated: C 56.23; H 6.29; S 12.51. % found: C 56.02; H 6.1; S 12.24.

c. Preparation of 2-phenylamino-6-methoxy-(1,2,3,4-tetrahydro-naphthalene (formula II; $R_3 = -OCH_3$).

This compound is prepared as described in Example 1(b). It is obtained by distillation at 171°–175°C/0.25 mm with a yield of 60 %.

After distillation, crystals of the product are obtained. By recrystallization from petroleum ether (60°–80°C) of from isopropanol, the product melts at 59°–61°C.

Analysis: % calculated: C 80.59; H 7.56; N 5.53. % found: C 80.66; H 7.33; N 5.90.

d. Preparation of the fumarate of 2-[N-phenyl-N-(γ-diethylaminopropyl)]-amino-6-methoxy-(1,2,3,4-tetrahydronaphthalene (formula I; n = 2; X = $H_2$; $R_1 = R_2 = -C_2H_5$; $R_3 = -OCH_3$).

This compound is prepared in the manner described in Example 1(c). In this case, on obtains 12.3 grams of an oil which is directly converted into fumarate (12.9 grams; yield: 78 %). After recrystallization from isopropanol, the fumarate melts at 164°–167°C.

Analysis: % calculated: C 69.68; H 7.93; N 5.8. % found: C 69.3; H 7.76; N 6.14.

EXAMPLE 3

Preparation of the fumarate of 2-[N-phenyl-N-(β-dimethylaminoethyl)]-amino-6-methoxy-(1,2,3,4-tetrahydronaphthalene) (formula I; n = 1; X = $H_2$; $R_1 = R_2 = -CH_3$; $R_3 = -OCH_3$).

0.034 mol of 2-phenylamino-6-methoxy-(1,2,3,4-tetrahydronaphthalene) in 70 ml of toluene are treated by 0.068 mol of NaNH$_2$. The sodium salt is obtained by boiling in toluene. 0.041 mol of β-chloroethyldimethylamine are then added and the obtained mixture is refluxed during 5 hours.

The desired compound is then obtained in the manner described in Example 1(c). The free amine (7.4 grams) is obtained by distillation at 189°–190°C/0.1 mm. The fumarate of this amine is prepared in an aqueous solution. After evaporation to dryness, the residue is recrystallized from isopropanol. Melting point: 174°–176°C.

Analysis: % calculated: C 68.16; H 7.32; N 6.36. % found: C 68.40; H 7.10; N 6.62.

EXAMPLE 4

Preparation of the fumarate of 2-[N-phenyl-N-(γ-dimethylaminepropyl)]-amino-6-methoxy-(1,2,3,4-tetrahydronaphthalene) (formula I; n = 2; X = H$_2$ ; R$_1$ = R$_2$ = —CH$_3$; R$_3$= —OCH$_3$).

This compound is prepared as described in Example 3, using γ-chloropropyldimethylamine instead of β-chloroethyldimethylamine. dimethylamine. The free amine is obtained by distillation at 185°–190°C/0.7 mm.

The fumarate is prepared in the usual way. After crystallization from a mixture of acetone and methanol, it melts at 133°–135°C.

Analysis: % calculated : C 68.70; H 7.54; N 6.16. % found : C 68.83; H 7.28; N6.28.

EXAMPLE 5

Preparation of the fumarate of 2-[N-phenyl-N-(β-diethylaminoethyl)]-amino-6-methoxy-(1,2,3,4-tetrahydronaphthalene) (formula I; n = 1; X = H$_2$; R$_1$ = R$_2$ = —C$_2$H$_5$; R$_3$ = —OCH$_3$).

This compound is prepared as described in Example 1(c) using β-chloroethyldiethylamine instead of γ-chloropropyldiethylamine. After recyrstallization from isopropanol, the desired compound melts at 158°–160°C.

Analysis: % calculated: C 69.20; H 7.74; N 5.97. % found: C 68.95; H 7.03; N 6.13.

EXAMPLE 6

Preparation of the fumarate of 2-[N-phenyl-N-(β-piperidineethyl)]-amino-6-methoxy-(1,2,3,4-tetrahydronaphthalene) (formula I; n = 1; X = H$_2$;

= piperidine; R$_3$ = —OCH$_3$).

This compound is prepared as described in Example 1(c). using β-chloroethylpiperidine instead of γ-chloropropyldiethylamine. After recrystallization from isopropanol, the obtained fumerate melts at 172°–174°C.

Analysis: % calculated: C 69.67; H 7.55; N 5.83. % found: C 70.59; H 7.78; N 5.62.

EXAMPLE 7

Preparation of the hydrochloride of 2-[N-phenyl-N-(γ-dimethylaminopropyl)]-amino-(1,2,3,4-tetrahydronaphthalene) (formula I; n = 2; X = H$_2$; R$_1$ =R$_2$ = —CH$_3$; R$_3$ = H).

This compound is prepared as described in Example 1(c), using γ-chloropropyldimethylamine. After recrystallization in a mixture of acetone and ether or in ethyl acetate, the desired hydrochloride melts at 146°–148°C.

Analysis: % calculated: C 73.12; H 8.47; N 8.12; Cl 10.28. % found: C 73.17; H 8.27; N 7.95; Cl 10.33.

EXAMPLE 8

Preparation of the hydrochloride of 2-[N-phenyl-N-(β-diethylaminoethyl)]-amino-(1,2,3,4-tetrahydronaphthalene) (formula I; n = 1; X = H$_2$; R$_1$ = R$_2$ = —C$_2$H$_5$; R$_3$ = H).

This compound is prepared in the manner described in Example 1(c), using β-chloroethyldiehylamine. After recrystallization from isopropanol, the obtained hydrochloride melts at 177°–179°C.

Analysis: % calculated: C 73.61; H 8.7; N 7.8; Cl 9.88. % found: C 73.52; H 8.55; N 7.92; Cl 9.96.

EXAMPLE 9

Preparation of the fumarate of 2[N-phenyl-N-(γ-pyrrolidinopropyl)]-amino-(1,2,3,4-tetrahydronaphthalene) (formula I; n = 2; X = H$_2$;

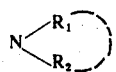

= pyrrolidine; R$_3$ = H).

Using γ-chloropropylpyrrolidine, this compound is prepared as described in Example 1(c). After recrystallization from isopropanol, the fumarate melts at 157–160°C.

Analysis: % calculated: C 71.97; H 7.6; N 6.21. % found: C 72.29; H 7.67; N 6.24.

EXAMPLE 10

Preparation of the hydrochloride of 2-[N-phenyl-N-(γ-piperidinopropyl)]-amino-(1,2,3,4-tetrahydronaphthalene) (formula I; n = 2; X = H$_2$;

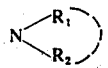

= piperidino; R$_3$ = H).

Using the method described in Example 1(c), except that γ-chloropropylpiperidine is used instead of γ-chloropropyldiethylamine, the desired hydrochloride is obtained. Melting point: 248°–250°C, after recrystallization from methanol.

EXAMPLE 11

Preparation of the hydrochloride of 2-[N-phenyl-N-(β-ethylaminopropionyl)]-amino-(1,2,3,4-tetrahydronaphthalene) (formula I; n = 2; X = 0; R$_1$ = H; R$_2$ = C$_2$H$_5$; R$_3$ = H).

a. Preparation of 2-[N-phenyl-N-(β-chloropropionyl]-amino-(1,2,3,4-tetrahydronaphthalene) (formula I; n = 2; Hal = Cl; R$_3$ = H).

0.1 mol of 2-phenylamino-1,2,3,4-tetrahydronaphthalene, 0.15 mol of the chloride of β-chloropropionic acid and 25 ml of benzene are refluxed during 4.5 hours. The solvent and the reagent excess are then removed. The residue is recrystallized from petroleum ether. M.P. 78°–81°C.

Analysis: % calculated: C 72.71; H 6.42; N 4.46; Cl 11.30. % found: C 72.39; H 6.10; N 4.46; Cl 11.21.

b. Preparation of the hydrochlirde of 2-[N-phenyl-N-(β-ethylaminopropionyl)]-amino-(1,2,3,4-tetrahydronaphthalene)

9.39 g (0.03 mol) of 2-[N-phenyl-N-(β-chloropropionyl)]amino-(1,2,3,4-tetrahydronaphthalene) are dissolved in 40 ml of ethanol. To the obtained solution, 50 ml of a 21.5 % solution of ethylamine in ethanol are added. The reaction mixture is heated in an autoclave at 110°C during 24 hours. After cooling, the mixture is treated with 80 ml of water and 20 ml of 1N NaOH and extracted with chloroform. The chloroform phase is then dried. After removal of the chloroform, the residue is treated with ether and a stream of dry hydrochloric acid is bubbled in the ether solution. After recrystallization from a mixture of methanol and ether, the hydrochloride melts at 204°–206°C.

Analysis: % calculated: C 70.28; H 7.58; N 7.80; Cl 9.88. % found : C 70.41; H 7.53; N 7.99; Cl 9.89.

EXAMPLE 12

Preparation of the hydrochloride and of the fumarate of 2-[M-phenyl-N-(γ-ethylaminopropyl)]-amino-(1,2,3,4-tetrahydronaphthalene) (formula I; $n = 2$; $X = H_2$; $R_1 = H$; $R_2 = C_2H_5$; $R_3 = H$).

6 g of 2-[N-phenyl-N-(β-ethylaminopropionyl)]-amine-(1,2,3,4-tetrahydronaphthalene), prepared as described in Example 11, are dissolved in 200 ml of anhydrous ether. The obtained solution is added drop by drop to a suspension of 1.06 g (1.5 equivalents) of lithium aluminum hydride (AlLiH$_4$) in 60 ml of anhydrous ether. The reaction mixture is refluxed under nitrogen during 2 hours. After cooling to 0°C, the excess of hydride and the complex are destroyed by means of ice. The medium is then extracted two times with 100 ml of ether. The ether phases are dried and part of the ether is removed, until the volume of the ether solution is 200 ml. A stream of hydrochloric acid is then bubbled through the concentrated ether solution. The obtained dihydrochloride is recrystallized from acetone.

The dihydrochloride is dissolved in water and the pH is adjusted to 6. The monohydrochloride is extracted by means of chloroform. After drying and filtration of the chloroform solution, the chloroform is removed. The residue is recrystallized from ethyl acetate. M.P. 128°–130°C.

Analysis of monohydrochloride: % calculated: C 73.12; H 8.47; N 8.12; Cl 10.28. % found: C 73.19; H 8.25; N 8.22; Cl 10.17.

The fumarate of the same compound prepared in a known manner melts at 152-154°C after recrystallization from isopropanol.

Analysis of the fumarate: % calculated: C 70.73; H 7.59; N 6.6. % found: C 70.73; H 7.43; N 6.7.

EXAMPLE 13

Preparation of 2-[N-phenyl-N-(β-methylaminopropionyl)]-amino-(1,2,3,4-tetrahydronaphthalene) (formula I; n = 2; X = 0; $R_1 = H$; $R_2 = CH_3$; $R_3 = H$).

This compound is prepared as described in Example 11(b), using methylamine instead of ethylamine. The desired compound is recrystallized from cyclohexane. M.P. 105°–107°C.

Analysis: % calculated: C 77.88; H 7.84; N 9.08. % found: C 77.72; H 7.77; N 9.20.

EXAMPLE 14

Preparation of the fumarate of 2-[N-phenyl-N-(γ-methylaminopropyl)]-amino-(1,2,3,4-tetrahydronaphthalene) (formula I; $n = 2$; $X = H_2$; $R_1 = H$; $R_2 = -CH_3$; $R_3 = H$).

This compound is prepared in the manner described in Example 12, by reduction of the 2-[N-phenyl-N-(β-methylaminopropionyl)]-amino-(1,2,3,4-tetrahydronaphthalene) prepared in Example 13, by means of lithium aluminum hydride. After recrystallization from a mixture of methanol and acetone, the obtained fumarate melts at 156°–157°C.

Analysis ($C_{22}H_{28}N_2O_2$: amine + ½ fummaric acid) % calculated: C 74.96; H 8.00; N 7.94. % found: C 75.32; H 8.02; N 8.22.

EXAMPLE 15

Preparation of 2-[N-phenyl-N-(β-dimethylaminoacetyl)]-amino-6-methoxy-(1,2,3,4-tetrahydronaphthalene) (formula I; $n = 1$; $X = 0$; $R_1 = R_2 = -CH_3$; $R_3 = -OCH_3$).

a. Preparation of 2-(N-phenyl-N-chloroacetyl)-amino-6-methoxy-(1,2,3,4-tetrahydronaphthalene) (formula V; $n = 1$; $R_3 = -OCH_3$)

0.01 mol of 2-phenylamino-6-methoxy-(1,2,3,4-tetrahydronaphthalene) and 0.015 mol of chloroacetic acid chloride are boiled in 25 ml of benzene during 4.5 hours. The solvent is then evaporated and the residue is recrystallized from cyclohexane. Melting point: 118°–120°C.

Analysis: % calculated: C 69.19; H 6.11; N 4.24; Cl 10.75. % found: C 69.0; H 5.90; M 4.14; Cl 10.6.

b. Preparation of 2-[H-phenyl-N-(β-dimethylaminoacetyl)]-amino6-methoxy-(1,2,3,4-tetrahydronaphthalene)

This compound is prepared by reacting 2-(N-phenyl-N-chloroacetyl)-amino-6-methoxy-(1,2,3,4-tetrahydronaphthalene) prepared in section (a) of this Example with dimethylamine, as described in Example 11(b).

EXAMPLE 16

Preparation of 2-[N-phenyl-N-(β-dimethylaminoethyl)]-amino-6-methoxy-(1,2,3,4-tetrahydronaphthalene) (formula I; n = 1; $X = H_2$; $R_1 = R_2 = -CH_3$; $R_3 = -OCH_3$).

This compound is prepared by reduction of the 2-[N-phenyl-N-(β-dimethylaminoacetyl)]-amino-6-methoxy-(1,2,3,4-tetrahydronaphthalene) prepared in Example 15, by means of lithium aluminum hydride, as described in Example 12.

EXAMPLE 17

Preparation of
2-[N-phenyl-N-(γ-diethylaminopropionyl)]-amino6-methoxy-(1,2,3,4-tetrahydronaphthalene) (formula I; $n = 2$; $X = 0$; $R_1 = R_2 = -C_2H_5$; $R_3 = -OCH_3$).

a. Preparation of
2-[N-phenyl-N-(β-chloropropionyl)]-amino-6-methoxy-(1,2,3,4-tetrahydronaphthalene) (formula V; $n = 2$; $R_3 = -OCH_3$).

This compound is prepared by the method described in Example 15(a), using β-chloropropionic acid chloride instead of chloroacetic acid chloride. After crystallization from cyclohexane, the product melts at 62–65°C.

Analysis: % calculated: C 69.86; H 6.45; N 4.07; Cl 10.3. % found: C 69.70; H6.38; N 4.12; Cl 10.1.

b. Preparation of
2-[N-phenyl-N-(γ-diethylaminopropionyl)]amino-6-methoxy-(1,2,3,4-tetrahydronaphthalene).

This compound is prepared by reacting 2-[N-phenyl-N-(β-chloropropionyl)]-amino-6-methoxy-(1,2,3,4-tetrahydronaphthalene) prepared in section (a) of this Example with diethylamine, by the method described in Example 11(b).

EXAMPLE 18

Preparation of
2-[N-phenyl-N-(γ-diethylaminopropyl)]-amino-6-methoxy-(1,2,3,4-tetrahydronaphthalene) (formula I; $n = 2$; $X = H_2$; $R_1 = R_2 = -C_2H_5$; $R_3 = -OCH_3$).

This compound is prepared by reduction of 2-[N-phenyl-N-(γdiethylaminopropylonyl)]-amino-6-methoxy-(1,2,3,4-tetrahydronaphthalene) prepared in Example 17, by means of lithium aluminum hydride, according to the method described in Example 12.

The following Examples 19 to 22 illustrate pharmaceutical compositions of this invention for the treatment of heart arrhythmy.

EXAMPLE 19

| CAPSULE | |
|---|---|
| Active ingredient of formula I | 100 mg |
| Lactose | 120 mg |
| Rice starch | 30 mg |
| Corn starch | 30 mg |
| Colloidal silica | 1 mg |
| | for one capsule |

EXAMPLE 20

| TABLET | |
|---|---|
| Active ingredient of formula I | 200 mg |
| Potato starch | 120 mg |
| Lactose | 80 mg |
| Starch sodium glycollate | 30 mg |
| Colloidal silica | 15 mg |
| Magnesium stearate | 5 mg |
| Hydroxy propylcellulose | 4 mg |
| Stearic acid | 2 mg |
| | for one tablet |

EXAMPLE 21

| PILLS. | |
|---|---|
| Core: | |
| Active ingredient of formula I | 50.0 mg |
| Lactose | 67.5 mg |
| Mycrocrystalline cellulose | 32.0 mg |
| Starch sodium glycollate | 8.2 mg |
| Colloidal silica | 0.4 mg |
| Magnesium stearate | 0.9 mg |
| Coating: | |
| Shellac | 1.0 mg |
| Sandarac | 0.2 mg |
| Castor oil | 0.3 mg |
| Gum arabic | 7.0 mg |
| Talc | 11.2 mg |
| Corn starch | 1.0 mg |
| Titanium oxide | 1.3 mg |
| Dyestuff | 4.0 mg |
| Sucrose | 142.8 mg |
| White wax/Carnauba wax | 0.2 mg |
| | for one pill |

EXAMPLE 22

| Solution for perfusion | |
|---|---|
| Active ingredient of formula I | 200 mg |
| Anhydrous sodium sulfite | 60 mg |
| Anhydrous sodium metabisulfite | 140 mg |
| Sodium chloride | 1.7 mg |
| Water for injection | ad 200 ml |

We claim:

1. A derivative of 2-amino(1,2,3,4-tetrahydronaphthalene) of the formula:

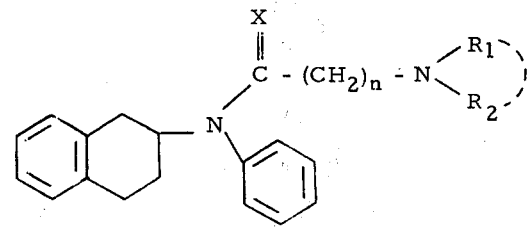

(I)

in which $n = 1$ or $2$, X represents two hydrogen atoms or one oxygen atom, $R_1$ and $R_2$ form together with the attached nitrogen atom a morpholino, piperidino, pyrrolidino or piperazino ring, with the proviso that $R_1$ may also represent hydrogen, and $R_3$ represents hydrogen or a lower alkoxy group, as well as the pharmaceutically acceptable acid addition salts of said compounds of formula (I).

* * * * *